United States Patent [19]

Yoshikawa et al.

[11] Patent Number: 5,013,848
[45] Date of Patent: May 7, 1991

[54] AROMATIC BISMALEIMIDE DERIVATIVES AND PROCESS FOR PREPARING SAME

[75] Inventors: Yukihiro Yoshikawa, Zushi; Midori Yamazaki, Hiratsuka; Keizaburo Yamaguchi, Kawasaki; Kenichi Sugimoto; Yoshimitsu Tanabe, both of Yokohama; Akihiro Yamaguchi, Kamakura, all of Japan

[73] Assignee: Mitsui Toatsu Chemicals, Incorporated, Tokyo, Japan

[21] Appl. No.: 87,255

[22] PCT Filed: Dec. 18, 1986

[86] PCT No.: PCT/JP86/00641
  § 371 Date: Jul. 22, 1987
  § 102(e) Date: Jul. 22, 1987

[87] PCT Pub. No.: WO87/03871
  PCT Pub. Date: Jul. 2, 1987

[30] Foreign Application Priority Data

Dec. 26, 1985 [JP] Japan ............................ 60-292087
Dec. 27, 1985 [JP] Japan ............................ 60-292881
Dec. 27, 1985 [JP] Japan ............................ 60-292882

[51] Int. Cl.$^5$ ............................ C07D 207/452
[52] U.S. Cl. ............................ 548/522; 548/521; 548/461; 548/549
[58] Field of Search .......... 548/461, 549, 521, 522

[56] References Cited

U.S. PATENT DOCUMENTS 4,376,206 3/1983 Oba et al. .................. 548/546
4,460,783 7/1984 Nishikawa et al. ............ 548/549
4,691,025 9/1987 Domeier .................... 548/521

FOREIGN PATENT DOCUMENTS 0028937 2/1980 Japan .

OTHER PUBLICATIONS

Morrison and Boyd, *Organic Chemistry*, 3rd ed. 1973, pp. 734–738.

*Primary Examiner*—Robert A. Wax
*Assistant Examiner*—Frederick F. Tsung
*Attorney, Agent, or Firm*—Fisher, Christen & Sabol

[57] ABSTRACT

A novel aromatic bismaleimide of the formula (I):

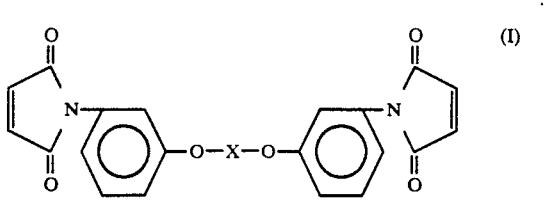

wherein X is

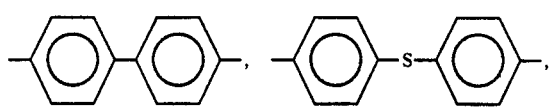

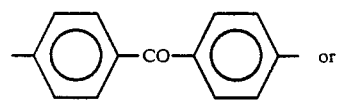 or

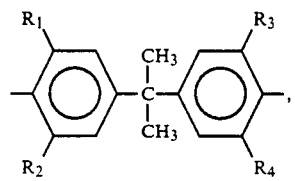

where $R_1$ $R_2$, $R_3$ and $R_4$ are a hydrogen atom or a methyl group. The bismaleimide is prepared by reacting an aromatic diamine having the formula (II):

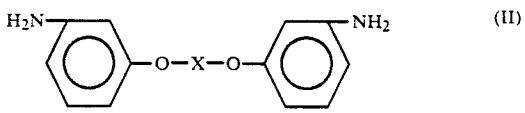

wherein X is the same as in the formula (I), with maleic anhydride and then conducting the ring-closing reaction of the resultant aromatic bismaleamic acid.

1 Claim, No Drawings

AROMATIC BISMALEIMIDE DERIVATIVES AND PROCESS FOR PREPARING SAME

TECHNICAL FIELD

The present invention relates to aromatic bismaleimide derivatives useful as the monomer of high temperature resistant polymers and the method for preparing the same.

BACKGROUND ART

Heretofore, thermosetting resins having imide structure have been widely used in industry due to their excellent properties such as electrical insulation, high-temperature stability and dimensional stability of molded articles.

Particularly, the thermosetting resin derived from aromatic bismaleimide is an insoluble and infusible material having excellent high-temperature stability. However, it has drawbacks of inferior impact resistance and poor flexibility.

Therefore, as a method for improving the impact strength and flexibility of the resin derived from aromatic bismaleimide, aromatic bismaleimide was tried to use in combination with aromatic diamines. For example, polyamino-bismaleimide resin (trade mark KERIMIDE, a product from Rhône-Poulenc Ind.) has impact strength and flexibility superior to the resin from aromatic bismaleimide alone. Thus the former resin is widely used for impregnation varnish, laminated boards, molded articles etc.

The above thermosetting resins, however, have been still unsatisfactory in the impact strength and flexibility viewpoint.

Therefore, monomers have not yet been provided for the thermosetting resins being satisfied with these properties.

DISCLOSURE OF THE INVENTION

An object of this invention is to provide novel and useful aromatic bismaleimide derivatives being useful as the raw material for the aromatic bismaleimide type thermosetting resin which is widely employed in industry in recent years.

Another object of this inventions is to provide novel and useful aromatic bismaleimide derivatives being useful as the raw material for the aromatic bismaleimide type thermosetting resin which is excellent in impact strength, flexibility and toughness.

This invention provides the following aromatic bismaleimide derivative:

An aromatic bismaleimide derivative represented by the formula (I):

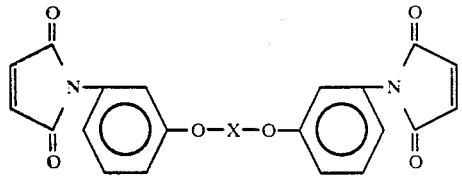

wherein X is (structures shown: biphenyl; diphenyl sulfide; diphenyl ketone; or 2,2-diphenylpropane with R1, R2, R3, R4 substituents)

where $R_1$, $R_2$, $R_3$ and $R_4$ are a hydrogen atom or a methyl group.

This invention also provides the following process for preparing the above aromatic bismaleimide derivative:

A process for preparing the aromatic bismaleimide derivative having the formula (I) which comprises reacting an aromatic diamine having the formula (II):

$$H_2N-\text{[aryl]}-O-X-O-\text{[aryl]}-NH_2 \quad (II)$$

wherein X is the same as in the formula (I), with maleic anhydride and then ring-closing resultant aromatic bismaleamic acid.

The aromatic bismaleimides represented by the aforementioned formula are novel compounds. The aromatic bismaleimide resins derived from these novel aromatic bismaleimides as the monomer, have excellent impact strength, flexibility and toughness in addition to the characteristics of conventional thermosetting resins.

THE BEST MODE FOR CARRYING OUT THE INVENTION

The ether-linkage containing diamines of the formula (II) are employed as the materials for preparing the novel aromatic bismaleimide derivatives of this invention.

The diamines include, for example, 4,4'-bis(3-aminophenoxy)biphenyl, 4,4'-bis(3-aminophenoxy)-diphenyl sulfide, 4,4'-bis(3-aminophenoxy)benzophenone, 2,2-bis[4-(3-aminophenoxy)phenyl]propane, 2,2-bis[3-methyl-4-(3-aminophenoxy)phenyl]propane, 2,2-bis[3,5-dimethyl-4-(3-aminophenoxy)phenyl]propane, 2-[3,5-dimethyl-4-(3-aminophenoxy)phenyl]-2-[4-(3-aminophenoxy)phenyl]propane, and 2-[3-methyl-4-(3-aminophenoxy)phenyl]-2-[4-(3-aminophenoxy)phenyl]propane, and the like.

These ether linkage containing diamines are those having amino groups located at m-positions to the ether linkages. These diamines can be favorably prepared by the following method which was found by the inventors of the present invention.

These diamines are prepared by condensing m-dinitrobenzene with dihydroxy compounds and then reducing the resultant intermediates.

In particular, a dihydroxy compound having the formula (III):

HO—X—OH  (III)

wherein X is the same as in the formula (I), is condensed with m-dinitrobenzene in an aprotic polar solvent in the presence of a base to obtain bis(3nitrophenoxy) compound of the formula (IV):

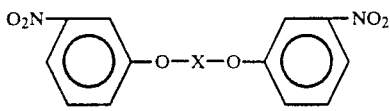

wherein X is the same as in the formula (I), and then reducing the compound, the aromatic diamine of the formula (II):

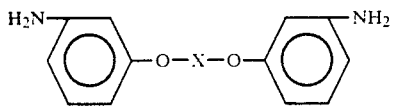

wherein X is the same as in the formula (I), can be industrially and advantageously prepared in a high purity and high yield.

The dihydroxy compounds having the formula (III) include, for example,
4,4'-dihydroxybiphenyl,
4,4'-dihydroxydiphenyl sulfide,
4,4'-dihydroxybenzophenone,
2,2-bis(4-hydroxyphenyl)propane,
2,2-bis(3-methyl-4-hydroxyphenyl)propane,
2,2-bis(3,5-dimethyl-4-hydroxyphenyl)propane,
2-(3,5-dimethyl-4-hydroxyphenyl)-2-(4-hydroxyphenyl)propane,
2-(3-methyl-4-hydroxyphenyl)-2-(4-hydroxyphenyl)propane, and the like.

The quantity of m-dinitrobenzene used is approximately 1.5-4.0 moles per mole of the dihydroxy compound.

The bases in use include, for example, potassium carbonate, potassium hydrogen carbonate and sodium carbonate. These bases are used in quantity of 1.5-3 moles per mole of the dihydroxy compounds.

The aprotic polar solvents include, for example, N,N-dimethylformamide, dimethylsulfoxide, 1-methyl-2-pyrrolidinone and 1,3-dimethyl-2-imidazolidinone. These solvents are used in 2-10 times by weight of the raw materials.

The reaction temperature is in the range of 120°-180° C. and the reactions time is in the range of 1-30 hours.

Catalytic reduction is preferable for industrially reducing bis(3-nitrophenoxy) intermediate. 3-5% palladium/active carbon is employed as the catalyst in quantity of 1-5% by weight of bis(3-nitrophenoxy) intermediate.

The solvents for the reaction include, for example, alcohols such as methanol, ethanol, isopropyl alcohol and butyl alcohol, and ethers such as 2-methoxyethanol and 2-ethoxyethanol. The quantity in use of these solvents is 3-10 times by weight of the bis(3-nitrophenoxy) compound.

The reaction temperature is in the range of 20°-100° C. After the completion of reaction, the diamines of the formula (II) can be obtained in a high purity and good yield by the usual post treatment.

In order to prepare the aromatic bismaleimide derivatives of this invention, a diamine of the formula (II) is in the first step, reacted with maleic anhydride in organic solvents to prepare bismaleamic acids having the formula (V):

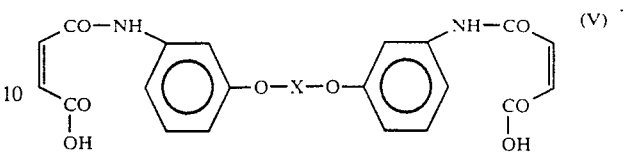

wherein X is the same as in the formula (I).

Although known methods can be applied for the reaction and are not restricted in particular, the following method can be used:

The quantity of maleic anhydride used is preferably 2-5 moles, more preferably 2.1-3 moles per mole of aromatic diamines.

The reaction is normally carried out in solvents. The solvents employed include, for example, halogenated hydrocarbons such as chloroform, methylene chloride, dichloroethane and trichloroethylene; ketones such as acetone, methyl ethyl ketone, cyclohexanone and diisopropyl ketone; ethers such as diethyl ether, tetrahydrofuran, dioxane and 2-methoxy ethanol; aromatic solvents such as benzene, toluene and chlorobenzene; and aprotic polar solvents such as acetonitrile, N,N-dimethylformamide, N,N-dimethylacetamide, dimethylsulfoxide, 1-methyl-2-pyrrolidinone and 1,3-dimethyl-2-imidazolidinone. Ketones are preferably used among these solvents.

The quantity in use of these solvents is not restricted in particular and normally 1-20 times by weight, preferably 3-10 times by weight of the raw materials.

The reaction temperature is in the range of 0°-120° C., preferably 10°-40° C.

Bismaleamic acid formed separates as a precipitate and the reaction mixture turns into a slurry. By filtering the precipitate, bismaleamic acid can be obtained in a high yield.

In the method of this invention, bismaleamic acid being formed as the intermediate is not always required to isolate for the successive preparation of bismaleimide. The ring-closing dehydration can be carried out in the same solvent as is to obtain bismaleimide.

In the next step, the bismaleamic acid thus obtained is subjected to the ring-closing dehydration in order to form bismaleimide of the formula (I). Acetic anhydride is used as the dehydrating agent for the ring-closure and the reaction is conducted in organic solvents in the presence of bases and catalysts.

The quantity of acetic anhydride in use is not less than two moles per mole of bismaleamic acid. Although the upper limit is not restricted in particular, the range of 2-4 moles per mole of bismaleamic acid is normally preferable.

The catalysts employed include, for example, oxides of alkali earth metals, and carbonates, sulfates, phosphates and acetates of iron (II and III), nickel (II), manganese (II and III), copper (I and II) or cobalt (II and III). Particularly preferred are nickel (II) acetate, Co (II) acetate and magnesium (II) oxide. These catalysts exhibit satisfactory effect even in a single use and combined use of two and more catalysts is also allowed.

The quantity in use of the catalysts is in the range of $5 \times 10^{-4} - 0.1$ mole per mole of bismaleamic acid.

The bases employed are alkali metal acetates or tertiary amines and include, for example, sodium acetate, potassium acetate, trimethylamine, triethylamine and tributylamine. The quantity of the bases in use is preferably in the range of 0.05-1.1 moles per mole of bismaleamic acid.

The reaction temperature is in the range of 20°-80° C. and the reaction time is in the range of 0.5-9 hours.

After completing the reaction, separated crystals are filtered or poured into water or methanol to obtain crystals of the product.

Properties will be described as follows on the bismaleimide derivatives of this invention thus obtained.

Table 1 illustrates melting points and 5% weight decrease temperatures of bismaleimide derivatives of the present invention.

Any derivative has a 5% weight decrease temperature of higher than 400° C. and is high-temperature resistant.

Table 2 illustrates the solubility of bismaleimide derivatives of this invention in common organic solvents.

The solubility of derivative Nos. 2 and 3 in the common organic solvents is remarkably higher than that of N,N'-(4,4'-methylenediphenylene)bismaleimide which has so far been used as the raw material for the bismaleimide resin. Further, derivative No. 4 has a higher solubility in ether type solvents such as 1,4-dioxane. High-boiling and hygroscopic solvents such as N,N-dimethylacetamide and N,N-dimethylformamide are required for preparing prepolymer type conventional impregnation varnish from N,N'-(4,4'-methylenediphenylene)bismaleimide, because of its low solubility in organic solvents. On the other hand, organic solvent soluble bismaleimide of this invention enables to replace these solvents with volatile and low-boiling common organic solvents.

TABLE 1

| No. | Derivative Structural formula | Melting point (°C.) | 5% Weight decrease temperature (in air, °C.) |
|---|---|---|---|
| 1 | (structure) | 207-209 | 459 |
| 2 | (structure) | 64-67 | 434 |
| 3 | (structure) | 116-121 | 453 |
| 4 | (structure) | 161-164 | 447 |
| 5 | (structure) | 144-146 | 449 |

TABLE 1-continued

| No. | Derivative Structural formula | Melting point (°C.) | 5% Weight decrease temperature (in air, °C.) |
|---|---|---|---|
| 6 | [structure: bismaleimide with two tetramethyl-bisphenol-A-type bridging groups and phenoxy-maleimide termini] | 230–233 | 444 |
| 7 | [structure: bismaleimide with tetramethyl bisphenol A bridge and phenoxy-maleimide termini] | 151–154 | 440 |

TABLE 2

| Bismaleimide Solvent | Derivative No. 2 | 3 | 4 | Known bismaleimide (Note) |
|---|---|---|---|---|
| Acetone | 23 | 22 | 4 | 5 |
| Methyl ethyl ketone | >50 | 17 | 3 | 3 |
| Chloroform | 35 | 29 | 8 | 7 |
| 1,2-Dichloroethane | 34 | 24 | 9 | 7 |
| 1,4-Dioxane | >50 | 33 | 18 | 9 |
| Tetrahydrofuran | 40 | 32 | 18 | 6 |
| Anisole | 33 | <2 | 8 | <1 |
| Diglyme | 32 | 20 | 6 | <1 |
| Toluene | 32 | <2 | 2 | <1 |
| 1-Acetyl-2-ethoxyethanol | 9 | 10 | 2 | <1 |
| N,N-Dimethylacetamide | >50 | >50 | >50 | 23 |

(Note)
N,N'-(4,4'-methylenediphenylene)bismaleimide

Therefore, by employing the derivatives of the present invention for above uses, the problem of residual solvents which causes deterioration of laminated boards and molded articles can be solved, and furthermore favorable effect can be obtained for the improvement of workability and the saving of energy.

In addition, the derivatives can be employed by applying these characteristics for a wide use in various fields of industry as the materials for electric insulators, high-temperature adhesives and coatings which require unique function.

The method of this invention will be further illustrated with respect to the following examples, reference examples and comparative examples.

EXAMPLE 1

In a reaction flask equipped with a stirrer and a thermometer, 43.2 grams (0.44 mole) of maleic anhydride were charged with 130 grams of acetone and dissolved. A solution of 73.6 grams (0.2 mole) of 4,4-bis(3-aminophenoxy)biphenyl in 515 grams of acetone was added dropwise to the above maleic anhydride solution at room temperature and further stirred for three hours at 23°–27° C.. After completing the reaction, the separated crystals were filtered, washed with acetone and dried to obtain bismaleamic acid as yellow crystals.

Yield: 110.6 g (98.0%)
Melting point: 183°–185° C.

Elementary analysis (%)

|  | C | H | N |
|---|---|---|---|
| Calculated | 68.08 | 4.28 | 4.96 |
| Found | 68.51 | 4.06 | 5.06 |

IR (KBr, cm$^{-1}$): 1720 (carboxyl group), 660sh (amide linkage), 1255 (ether linkage)

The suspension of 112 grams of bismaleamic acid thus obtained in 300 grams of acetone was added with 9.6 grams of triethylamine and stirred for 30 minutes.

After adding 0.4 gram of magnesium (II) oxide and 0.04 gram of cobalt (II) acetate tetrahydrate, 52.0 grams of acetic anhydride were added dropwise for minutes at 25° C. and further stirred for three hours. After completing the reaction, the separated crystals were filtered, washed and dried to obtain bismaleimide (1) as light yellow crystals.

Yield: 84.5 g (80.0%)
Melting point: 207°–209° C.

Elementary analysis (%)

|  | C | H | N |
|---|---|---|---|
| Calculated | 72.72 | 3.81 | 5.30 |
| Found | 72.54 | 3.59 | 5.31 |

IR (KBr, cm$^{-1}$): 1770 and 1710 (imide linkage), 1250 (ether linkage)
MS (FD method, m/e): 528 (M$^+$)

EXAMPLE 2

In a reaction flask equipped with a stirrer and a thermometer, 37.8 grams (0.385 mole) of maleic anhydride were charged with 113 grams of acetone and dissolved. A solution of 70 grams (0.175 mole) of 4,4'-bis(3-aminophenoxy)diphenyl sulfide in 140 grams of acetone was added dropwise to the above maleic anhydride solution and stirred for three hours at 25° C.. The separated crystals were filtered, washed and dried to obtain bismaleamic acid as light yellow crystals.

Yield: 104 g (99.6%)
Melting point: 202°–204° C.

Elementary analysis (%)

|  | C | H | N | S |
|---|---|---|---|---|
| Calculated | 64.42 | 4.05 | 4.69 | 5.37 |
| Found | 64.35 | 3.94 | 4.61 | 5.25 |

IR (KBr, cm$^{-1}$): 3280 (NH), 1690 (carboxyl group), 1240 (ether linkage)

MS (FD method, m/e): 596 (M$^+$), 400

In a reaction vessel equipped with a stirrer and a thermometer, 104 grams of bismaleamic acid thus obtained were suspended in 300 grams of acetone.

After adding 8.4 grams of trietylamine, the resultant mixture was stirred for 30 minutes at 25° C.

After adding 0.35 gram of magnesium (II) oxide and 0.035 gram of cobalt (II) acetate tetrahydrate, 45.5 grams of acetic anhydride were added dropwise and further stirred for two hours at 25° C.

After completing the reaction, the reaction mixture was added dropwise to one liter of water with stirring. The separated crystals were filtered, washed with water and dried to obtain bismaleimide (2) as light yellow crystals.

Yield: 92 g (93.8%)

The crystals were recrystallized from acetone to obtain a pure product.

Melting point: 64°–67° C.

Elementary analysis (%)

|  | C | H | N | S |
|---|---|---|---|---|
| Calculated | 68.56 | 3.60 | 4.99 | 5.72 |
| Found | 68.48 | 3.53 | 4.80 | 5.95 |

IR (KBr, cm$^{-1}$): 1770sh and 1730 (imide linkage), 1260 (ether linkage)

MS (FD method, m/e): 560 (M$^-$)

EXAMPLE 3

In a reaction flask equipped with a stirrer and a thermometer, 37.8 grams (0.385 mole) of maleic anhydride were charged with 160 grams of acetone and dissolved. A solution of 70 grams (0.175 mole) of 4,4-bis(3-aminophenoxy)diphenyl sulfide in 140 grams of acetone was added dropwise and stirred for three hours at 25° C. to separate out crystals. After adding 8.4 grams of triethylamine, the mixture was stirred for 30 minutes at 25° C.. After adding 0.35 gram of magnesium (II) oxide and 0.035 gram of cobalt (II) acetate tetrahydrate, 45.5 grams of acetic anhydride were added dropwise and further stirred for two hours at 25° C..

The reaction mixture was added dropwise to one liter of water with stirring. The separated crystals were filtered, washed with water and dried to obtain bismaleimide (2) as light yellow crystals.

Yield: 94.2 g (96.0%)

EXAMPLE 4

In a reaction flask equipped with a stirrer and a thermometer, 43.2 grams (0.44 mole) of maleic anhydride were charged with 130 grams of acetone and dissolved. A solution of 79.3 grams (0.2 mole) of 4,4-bis(3-aminophenoxy)benzophenone in 396 grams of acetone was added dropwise to the above maleic anhydride solution at room temperature and further stirred for three hours at 23°–27° C.

After ending the reaction, the separated crystals were filtered, washed with acetone and dried to obtain bismaleamic acid as light yellow crystals.

Yield: 117 g (98.2%)
Melting point: 204°–205° C.

Elementary analysis (%)

|  | C | H | N |
|---|---|---|---|
| Calculated | 66.89 | 4.08 | 4.73 |
| Found | 67.15 | 4.08 | 4.66 |

IR (KBr, cm$^{-1}$): 3320 (NH), 1720 (carboxyl group), 1695 (amide linkage), 1630 (ketone), 1245 (ether linkage)

The suspension of 59.3 grams of bismaleamic acid thus obtained in 180 grams of acetone was added with 4.8 grams of triethylamine and stirred at room temperature. After adding 0.2 gram of magnesium (II) oxide and 0.02 gram of cobalt (II) acetate tetrahydrate, 26.0 grams of acetic anhydride were added dropwise for 30 minutes at 25° C. and further stirred for four hours.

After completing the reaction, the reaction mixture was added dropwise to one liter of water with stirring. The separated crystals were filtered, washed with water and dried to obtain bismaleimide (3) as yellow crystals.

Yield: 53.3 g (95.7%)

The crystals were recrystallized from acetone/ethanol to afford a pure product.

Melting point: 116°–121° C.

Elementary analysis (%)

|  | C | H | N |
|---|---|---|---|
| Calculated | 71.22 | 3.62 | 5.03 |
| Found | 71.86 | 3.52 | 5.28 |

IR (KBr, cm$^{-1}$): 1790 and 1700 (imide linkage), 1640 (ketone), 1240 (ether linkage)

MS (FD method, m/e): 556 (M$^-$)

EXAMPLE 5

In a reaction flask equipped with a stirrer and a thermometer, 10.8 grams (0.11 mole) of maleic anhydride were charged with 32 grams of acetone and dissolved. A solution of 20.5 grams (0.05 mole) of 2,2-bis[4-(3-aminophenoxy)phenyl]propane in 41 grams of acetone was added dropwise to the above maleic anhydride solution at room temperature and further stirred for three hours at 23°–27° C. After completing the reaction, the separated crystals were filtered, washed with acetone and dried to obtain bismaleamic acid as yellow crystals.

Yield: 29.7 g (90.8%)
Melting point : 169°–171° C.

Elementary analysis (%)

|  | C | H | N |
|---|---|---|---|
| Calculated | 69.30 | 4.98 | 4.62 |
| Found | 69.19 | 4.73 | 4.59 |

IR (KBr, cm$^{-1}$) 3280 and 3220 (NH), 1700 (carboxyl group), 1685 (amide linkage)

MS (FD method, m/e): 608 (M+2), 510, 491, 411

The suspension of 38 grams of bismaleamic acid thus obtained in 92 grams of acetone was added with 3 grams of triethylamine and stirred for 30 minutes at room temperature.

After adding 0.13 gram of magnesium (II) oxide and 0.013 gram of cobalt (II) acetate tetrahydrate, 16 grams of acetic anhydride were added dropwise for 30 minutes at 25° C. and further stirred for four hours.

After ending the reaction, the separated crystals were filtered, washed with methanol and dried at 40° C. under reduced pressure to obtain bismaleimide (4) as yellow crystals.

Yield: 30 g (83.9%)

Melting point: 161°–164° C.

Elementary analysis (%)

|  | C | H | N |
| --- | --- | --- | --- |
| Calculated | 73.68 | 4.59 | 4.91 |
| Found | 74.14 | 4.27 | 4.84 |

IR (KBr, cm$^{-1}$) 1775 and 1715 (imide linkage), 1255 (ether linkage)

MS (FD method, m/e): 571 (M+1)

EXAMPLE 6

In a reaction flask equipped with a stirrer and a thermometer, 21.6 grams (0.22 mole) of maleic anhydride were charged with 64 grams of acetone and dissolved. A solution of 41 grams (0.10 mole) of 2,2-bis[4-(3-aminophenoxy)phenyl]propane in 82 grams of acetone was added dropwise to the above maleic anhydride solution at room temperature and further stirred for three hours to separate out crystals.

After adding 4.7 grams of triethylamine, the reaction mixture was stirred for 30 minutes at room temperature.

After adding 0.21 gram of magnesium (II) oxide and 0.021 gram of cobalt (II) acetate tetrahydrate, 25.3 grams of acetic anhydride were added dropwise for 30 minutes at room temperature and further stirred for four hours. After completing the reaction, the separated crystals were filtered, washed with methanol and dried at 40° C. under reduced pressure to obtain bismaleimide (4) as light yellow crystals.

Yield: 55.1 g (96.5%)

EXAMPLE 7

In a reaction flask equipped with a stirrer and a thermometer, 2.16 grams (0.022 mole) of maleic anhydride were charged with 6.5 grams of acetone and dissolved. A solution of 4.38 grams (0.01 mole) of 2,2-bis[3-methyl-4-(3-aminophenoxy)phenyl]propane in 22 grams of acetone was added dropwise to the above maleic anhydride solution at room temperature and further stirred for three hours at 23°–27° C. After completing the reaction, the separated crystals were filtered, washed with acetone and dried to obtain bismaleamic acid as light yellow crystals.

Yield: 6.2 g (97.6%)

Melting point: 156°–159° C.

Elementary analysis (%)

|  | C | H | N |
| --- | --- | --- | --- |
| Calculated | 70.02 | 5.40 | 4.41 |
| Found | 69.89 | 5.50 | 4.45 |

IR (KBr, cm$^{-1}$): 720sh (carboxyl group), 1700 (amide linkage), 1250 (ether linkage)

The suspension of 2.8 grams of bismaleamic acid thus obtained in 8.4 grams of acetone was added with 0.21 gram of triethylamine and stirred for 30 minutes at room temperature.

After adding nine milligrams of magnesium (II) oxide and 0.9 milligram of cobalt (II) acetate tetrahydrate, 1.14 grams of acetic anhydride were added dropwise for 30 minutes at 25° C. and further stirred for four hours. After ending the reaction, the reaction mixture was added dropwise to 300 milliliters of water with stirring. The separated crystals were filtered, washed with water and dried to obtain bismaleimide (5) as yellow crystals.

Yield: 2.4 g (90.9%)

The crystals were recrystallized from acetone to obtain a pure product.

Melting point: 143.5°–145.8° C.

Elementary analysis (%)

|  | C | H | N |
| --- | --- | --- | --- |
| Calculated | 74.23 | 5.05 | 4.68 |
| Found | 73.86 | 5.02 | 4.66 |

IR (KBr, cm$^{-1}$): 1785 and 1705 (imide linkage), 1240 (ether linkage)

EXAMPLE 8

In a reaction flask equipped with a stirrer and a thermometer, 2.16 grams (0.022 mole) of maleic anhydride were charged with 6.5 grams of acetone and dissolved.

A solution of 4.67 grams (0.01 mole) of 2,2-bis[3,5-dimethyl-4-(3-aminophenoxy)phenyl]propane in 19 grams of acetone was added dropwise to the mixture at room temperature and further stirred for three hours at 23°–27° C.

After completing the reaction, the reaction mixture was added dropwise to 300 milliliters of water with stirring. The separated crystals were filtered, washed with water and dried to obtain bismaleamic acid as light yellow crystals.

Yield: 6.6 g (98.5%)

Melting point: 207.5°–209° C.

Elementary analysis (%)

|  | C | H | N |
| --- | --- | --- | --- |
| Calculated | 70.68 | 5.78 | 4.23 |
| Found | 70.67 | 6.02 | 4.25 |

IR (KBr, cm$^{-1}$): 3400 (NH), 720sh (carboxyl group), 1705 (amide linkage), 1245 (ether linkage)

The suspension of 2.6 grams of bismaleamic acid thus obtained in 7.8 grams of acetone was added with 0.19 gram of triethylamine and stirred for 30 minutes at room temperature.

After adding eight milligrams of magnesium (II) oxide and 0.8 milligram of cobalt (II) acetate tetrahydrate, 1.04 grams of acetic anhydride were added dropwise for 30 minutes at 25° C. and further stirred for four hours. After completing the reaction, the reaction mixture was added dropwise to 300 milliliters of water with stirring. The separated crystals were filtered, washed with water and dried to obtain bismaleimide (6) as light yellow crystals.

Yield: 2.3 g (93.5%)

The crystals were recrystallized from acetone to afford a pure product.

Melting point: 230°–233° C.

Elementary analysis (%)

|  | C | H | N |
|---|---|---|---|
| Calculated | 74.74 | 5.47 | 4.47 |
| Found | 74.49 | 5.34 | 4.38 |

IR (KBr, cm$^{-1}$): 1765sh and 1705 (imide linkage), 1235 (ether linkage)

EXAMPLE 9

In a reaction flask equipped with a stirrer and a thermometer, 2.16 grams (0.022 mole) of maleic anhydride were charged with 6.5 grams of acetone and dissolved. A solution of 4.38 grams (0.01 mole) of 2-[3,5-dimethyl-4-(3-aminophenoxy)phenyl]-2-[4-(3-aminophenoxy)-phenyl]propane in 12 grams of acetone was added dropwise to the mixture at room temperature and further stirred for three hours at 23°–27° C.

After completing the reaction, the reaction mixture was added dropwise to 300 milliliters of water with stirring. The separated crystals were filtered, washed with acetone and dried to obtain bismaleamic acid as light yellow crystals.

Yield: 6.3 g (99.4%)

Melting point: 143°–146° C.

Elementary analysis (%)

|  | C | H | N |
|---|---|---|---|
| Calculated | 70.02 | 5.40 | 4.41 |
| Found | 69.97 | 5.37 | 4.31 |

IR (KBr, cm$^{-1}$): 1710 (carboxyl group), 1695 (amide linkage), 1240 (ether linkage)

The suspension of 2.5 grams of bismaleamic acid thus obtained in five grams of acetone was added with 0.19 gram of triethylamine and stirred for 30 minutes at room temperature.

After adding eight milligrams of magnesium (II) oxide and 0.8 milligram of cobalt (II) acetate tetrahydrate, 1.04 grams of acetic anhydride were added dropwise for 30 minutes at 25° C. and further stirred for five hours.

After the end of the reaction, the reaction mixture was added dropwise to 300 milliliters of water with stirring. The separated crystals were filtered, washed with water and dried to obtain bismaleimide (7) as yellow crystals.

Yield: 2.2 g (93%)

The crystals were recrystallized from acetone/ethanol to obtain a pure product.

Melting point: 151.2°–154.4° C.

Elementary analysis (%)

|  | C | H | N |
|---|---|---|---|
| Calculated | 74.23 | 5.05 | 4.68 |
| Found | 74.50 | 4.82 | 4.64 |

IR (KBr, cm$^{-1}$): 1785 and 1705 (imide linkage), 1240 (ether linkage)

REFERENCE EXAMPLES 1-4

A stainless steel reaction vessel equipped with a stirrer, reflux condenser and nitrogen inlet tube was charged with N,N'-4,4'-bis(3-aminophenoxy)biphenyl-bismaleimide and 4,4'-diaminodiphenylmethane at a molar ratio shown in Table 3, and reaction was carried out at 180° C. for 20 minutes in a fused state. The reaction mixture was then cooled to room temperature. Brown transparent and glassy solid product was broken and taken out from the reaction vessel. The product was further ground in a mortor and passed through a 60 mesh sieve to give a composition of partially cured polyaminobismaleimide type thermosetting resin.

The composition thus obtained was charged into a mold having a dimension of 10×80×4 mm and being previously heated to 180° C., followed by compressing under a pressure of 50 kg/cm$^2$ at 200° C. for 30 minutes. After cooling to room temperature, the compression molded article was taken out from the mold and further post-cured at 250° C. for four hours in a hot air gear oven to give specimens for testing Izod impact strength and flexural strength. Izod impact strength (unnotched) and flexural strength were measured in accordance with ASTM D-256 and ASTM D-790, respectively. At the same time, 5% weight decrease temperature was also determined. Results obtained are shown in Table 3.

REFERENCE EXAMPLE 5

A stainless steel reaction vessel equipped with a stirrer, reflux condenser and nitrogen inlet tube was charged with N,N'-4,4'-bis(3-aminophenoxy)-biphenyl-bismaleimide and 4,4'-diaminodiphenylmethane at a mole ratio shown in Table 3. N-Methyl-2-pyrrolidone was added to this mixture in the quantity so as to obtain 55 weight percent of the resin concentration. After dissolving both components, the reaction was carried out at 130° C. for 50 minutes. Brown transparent varnish thus obtained was added dropwise to water with stirring. The separated precipitate was filtered, washed with water and dried with hot air at 80° C. for 15 hours. The product was ground in a mortor and passed through a 60 mesh sieve to obtain a composition of partially cured polyaminobismaleimide type thermosetting resin.

The procedure of Reference examples 1-4 was repeated to obtain results shown in Table 3.

REFERENCE EXAMPLES 6-8 AND COMPARATIVE EXAMPLES 1 AND 2

The procedure of Reference examples 1-4 was repeated by using bismaleimide and diamine shown in Table 3 at a mole ratio in Table 3. The results in Table 3 were obtained.

As is clear from the results shown in Table 3, the thermosetting resin composition of this invention is excellent in Izod impact strength and furthermore has high flexural strength and modulus. Therefore, the composition is a material having an excellent impact strength and flexibility. The material is also excellent in heat resistance as indicated by 5% weight decrease temperature of no less than 400° C.

TABLE 3

Reference examples 1-8 and Comparative examples 1 and 2

| Example | Bismaleimide (B) | Diamine (A) | Mole ratio (B/A) | Izod impact strength (unnoteched) (kg · cm/cm) | Flexural strength (kg/cm²) | Flexural modulus (kg/cm²) | 5% weight decrease temperature (°C.) |
|---|---|---|---|---|---|---|---|
| Reference 1 | N,N'-4,4'-bis(3-aminophenoxy)biphenylbismaleimide | 4,4'-diamino diphenylmethane | 8.0/1.0 | 13 | 980 | 37,100 | 421 |
| Reference 2 | N,N'-4,4'-bis(3-aminophenoxy)biphenylbismaleimide | 4,4'-diamino diphenylmethane | 5.0/1.0 | 14 | 1020 | 36,200 | 418 |
| Reference 3 | N,N'-4,4'-bis(3-aminophenoxy)biphenylbismaleimide | 4,4'-diamino diphenylmethane | 2.0/1.0 | 16 | 1160 | 34,800 | 416 |
| Reference 4 | N,N'-4,4'-bis(3-aminophenoxy)biphenylbismaleimide | 4,4'-diamino diphenylmethane | 1.0/1.0 | 13 | 1000 | 34,200 | 402 |
| Reference 5 | N,N'-4,4'-bis(3-aminophenoxy)biphenylbismaleimide | 4,4'-diamino diphenylmethane | 2.0/1.0 | 15 | 1130 | 35,200 | 418 |
| Reference 6 | N,N'-1,3-bis(3-aminophenoxy)benzenebismaleimide | 4,4'-diamino diphenylmethane | 2.0/1.0 | 14 | 1210 | 34,600 | 416 |
| Reference 7 | N,N'-2,2-bis[4-(3-aminophenoxy)phenyl]propane-bismaleimide | 4,4'-diamino diphenylmethane | 2.0/1.0 | 13 | 990 | 35,800 | 407 |
| Reference 8 | N,N'-bis[4-(3-aminophenoxy)phenyl]sulfidebismaleimide | 4,4'-diamino diphenylmethane | 2.0/1.0 | 14 | 990 | 34,900 | 405 |
| Comparative 1 | N,N'-(4,4'-methylenediphenylene)bismaleimide | 4,4'-diamino diphenylmethane | 2.0/1.0 | 11 | 920 | 37,200 | 393 |
| Comparative 2 | N,N'-(4,4'-methylenediphenylene)bismaleimide | 4,4'-diamino diphenylmethane | 1.0/0 | 4 | 710 | 52,600 | 418 |

We claim:

1. An aromatic bismaleimide compound of the formula (I):

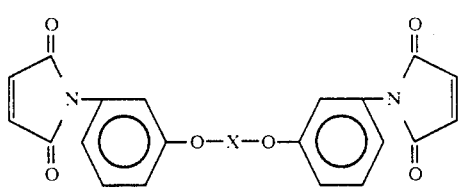

wherein X is

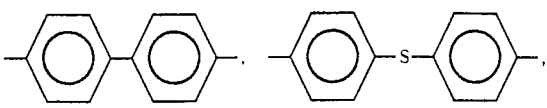

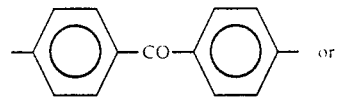

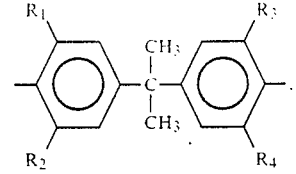

where $R_1$, $R_2$, $R_3$ and $R_4$ are hydrogen atom or a methyl group.

* * * * *